United States Patent
Park et al.

(10) Patent No.: US 11,724,125 B2
(45) Date of Patent: Aug. 15, 2023

(54) RADIOTHERAPY APPARATUS FOR ANIMAL

(71) Applicant: Korea Institute of Radiological & Medical Sciences, Seoul (KR)

(72) Inventors: Seung Woo Park, Seoul (KR); Mun Sik Choi, Gyeonggi-do (KR); Hae June Lee, Seoul (KR); Su Chul Han, Seoul (KR); Jong Hyun Back, Gyeongsangnam-do (KR)

(73) Assignee: Korea Institute of Radiological & Medical Sciences, Seoul (KR)

( * ) Notice: Subject to any disclaimer, the term of this patent is extended or adjusted under 35 U.S.C. 154(b) by 0 days.

(21) Appl. No.: 17/255,553

(22) PCT Filed: Apr. 17, 2019

(86) PCT No.: PCT/KR2019/004607
§ 371 (c)(1),
(2) Date: Dec. 23, 2020

(87) PCT Pub. No.: WO2020/004794
PCT Pub. Date: Jan. 2, 2020

(65) Prior Publication Data
US 2021/0268311 A1    Sep. 2, 2021

(30) Foreign Application Priority Data
Jun. 27, 2018 (KR) .................. 10-2018-0074185

(51) Int. Cl.
*A61N 5/10* (2006.01)
(52) U.S. Cl.
CPC ......... *A61N 5/1001* (2013.01); *A61N 5/1045* (2013.01); *A61N 5/1065* (2013.01);
(Continued)
(58) Field of Classification Search
None
See application file for complete search history.

(56) References Cited

U.S. PATENT DOCUMENTS

| 4,726,046 A | 2/1988 | Nunan |
| 6,353,655 B1 * | 3/2002 | Siochi ................. A61N 5/1031 378/65 |

(Continued)

FOREIGN PATENT DOCUMENTS

| JP | 2003-038475 A | 2/2003 |
| KR | 10-2002-0073955 A | 9/2002 |

(Continued)

OTHER PUBLICATIONS

International Search Report issued in corresponding International Patent Application No. PCT/KR2019/004607 dated Jul. 29, 2019.
Extended European Search Report issued in corresponding European Patent Application No. 19825088.8 dated Jul. 13, 2021.
Office Action issued in related Chinese Patent Application No. 201980043508.0 dated Jul. 5, 2022.
(Continued)

*Primary Examiner* — Hoon K Song
(74) *Attorney, Agent, or Firm* — Morgan, Lewis & Bockius LLP

(57) ABSTRACT

A radiotherapy apparatus for an animal comprises a treatment part including an accommodation space for placing an animal, an irradiation part including an electron generator and a linear accelerator coupled to one side of the electron generator and disposed in a direction perpendicular to the treatment part, the linear accelerator being configured to emit radiation toward the treatment part, and an image acquisition part located at a preset interval from the treatment part along an irradiation direction of the radiation and configured to obtain an image of an irradiation area when the radiation is applied, wherein the radiation has an output of 1 MeV to 2 MeV so as to be applied to a diseased part located within a predetermined distance range from epidermis of the animal.

6 Claims, 3 Drawing Sheets

(52) U.S. Cl.
CPC .... *A61N 5/1077* (2013.01); *A61N 2005/1022* (2013.01); *A61N 2005/1089* (2013.01)

(56) References Cited

U.S. PATENT DOCUMENTS

| | | | |
|---|---|---|---|
| 10,183,181 B2 | 1/2019 | Kawrykow et al. | |
| 10,485,993 B2 | 11/2019 | Goer et al. | |
| 10,821,304 B2 | 11/2020 | Kawrykow et al. | |
| 2004/0184579 A1 | 9/2004 | Mihara et al. | |
| 2009/0080602 A1* | 3/2009 | Brooks | A61B 6/4258 378/65 |
| 2011/0075815 A1 | 3/2011 | Brown et al. | |
| 2013/0158382 A1 | 6/2013 | Chao | |
| 2014/0037044 A1* | 2/2014 | Ning | G06T 7/0012 378/4 |
| 2017/0021198 A1 | 1/2017 | Kawrykow et al. | |
| 2019/0240511 A1 | 8/2019 | Kawrykow et al. | |

FOREIGN PATENT DOCUMENTS

| | | |
|---|---|---|
| KR | 10-0949141 B1 | 3/2010 |
| KR | 10-2014-0056083 A | 5/2014 |
| KR | 10-2018-0033224 A | 4/2018 |
| WO | 2017/151763 A1 | 9/2017 |

OTHER PUBLICATIONS

Expert Committee of the National Health Professional Technical Qualification Examinations, "Health Professional Technical Qualification Examination guidelines—image medical specialty of year 2003", Beijing: Knowledge Publishing House, Sep. 30, 2001, pp. 325-330 (see English statement of relevance).

Decision on Rejection issued in corresponding Chinese Patent Application No. 201980043508.0 dated Mar. 15, 2023.

Office Action issued in corresponding European Patent Application No. 19825088.8 dated Jun. 23, 2023.

* cited by examiner

RADIOTHERAPY APPARATUS FOR ANIMAL

TECHNICAL FIELD

Embodiments of the present disclosure relate to a radiotherapy apparatus for an animal, and more particularly, relate to a radiotherapy apparatus having radiation in an optimized MeV energy spectrum for treatment of an animal.

BACKGROUND ART

Recently, studies on radiotherapy for treatment of tumors and the like have been increasingly conducted. The radiotherapy refers to a method of retarding or stopping growth of malignant tissue or eliminating the malignant tissue by damaging or destroying target tissue by using high-energy waves such as X-rays or gamma rays, or high-energy particles such as electron rays or proton rays.

In general, studies on radiotherapy apparatuses for radiotherapy targeting humans have been conducted. The radiotherapy for humans refers to a therapy killing tumors, cancer cells, and the like by using high-energy radiation. Furthermore, radiotherapy for animals targets medium-sized animals, and animal cancer frequently occurs in epidermis in a current clinical practice.

Currently, in many animal hospitals around the world, radiotherapy apparatuses for humans are used for radiotherapy for animals.

A radiotherapy apparatus having high energy has efficiency in treatment of cancer located at an internal location as energy becomes higher, but requires a high radiation shielding level and is inefficient in the size of the apparatus and economic aspects for ensuring and operating a space.

Furthermore, a radioactive isotope treatment apparatus, such as Co-60, which uses gamma rays generated from radioactive isotopes has been most popularly used before the advent of a radiotherapy apparatus based on a linear accelerator, but has been decreasingly used due to a problem regarding safety management and security for an isotope source.

Accordingly, to satisfy gradually increasing demands for radiotherapy for an animal, a radiotherapy apparatus that has lower energy than a radiotherapy apparatus for a human, has energy with a small uncertain penumbra area, and ensures economical efficiency is required.

DISCLOSURE

Technical Problem

An aspect of the present disclosure provides a radiotherapy apparatus for an animal. The technical problems to be solved by the present disclosure are not limited to the aforementioned problems, and any other technical problems may be inferred from the following embodiments.

Technical Solution

A radiotherapy apparatus for an animal includes a treatment part including an accommodation space in which the animal is placed, an irradiation part including an electron generator and a linear accelerator that is coupled to one side of the electron generator and is disposed in a direction perpendicular to the treatment part and that emits radiation toward the treatment part, and an image acquisition part that is located at a preset interval from the treatment part along an irradiation direction of the radiation and that obtains an image of an irradiation area when the radiation is applied, and the radiation has an output of 1 MeV to 2 MeV so as to be applied to a diseased part located within a predetermined distance range from epidermis of the animal.

In an embodiment, the irradiation part may further include a lamp that measures the irradiation area when the irradiation is applied and an ion chamber that measures an output of the radiation, and the lamp and the ion chamber may be located on the same plane.

In an embodiment, the irradiation part may further include a first collimator and a second collimator that adjust the irradiation area of the radiation, and the second collimator may be a pin-hole collimator.

In an embodiment, the treatment part may be movable in a horizontal direction and a vertical direction with respect to a parallel surface of the ground.

In an embodiment, the image acquisition part may further include a reflecting mirror, and an angle between a parallel surface of the ground and the reflecting mirror may be 45° or less.

In an embodiment, the predetermined distance range may be a range of 10 cm to 20 cm.

In an embodiment, the radiotherapy apparatus may further include a beam stopper located to be spaced apart from the image acquisition part along the irradiation direction of the radiation to interrupt leakage of the radiation through any one of the treatment part or the image acquisition part.

Advantageous Effects

The present disclosure may provide a radiotherapy apparatus for an animal. Specifically, the radiotherapy apparatus according to the present disclosure may be a radiotherapy apparatus for an animal that includes a treatment part including an accommodation space in which the animal is placed, an irradiation part including an electron generator and a linear accelerator that is coupled to one side of the electron generator and is disposed in a direction perpendicular to the treatment part and that emits radiation toward the treatment part, and an image acquisition part that is located at a preset interval from the treatment part along an irradiation direction of the radiation and that obtains an image of an irradiation area when the radiation is applied, in which the radiation has an output of 1 MeV to 2 MeV so as to be applied to a diseased part located within a predetermined distance range from epidermis of the animal.

In this case, a problem regarding a high-level shielding apparatus required when a radiotherapy apparatus having high energy of 6 MeV or more is used and a problem regarding economical efficiency for ensuring and operating a space for operating the apparatus may be minimized.

Furthermore, the radiotherapy apparatus according to the present disclosure uses a low-energy spectrum and therefore has a structure in which vertical arrangement is made due to a short length and the ion chamber and the lamp included are located on the same plane. Thus, the size and volume of the radiotherapy apparatus may be minimized.

In addition, the radiotherapy apparatus according to the present disclosure adjusts the angle of the reflecting mirror included in the image acquisition part, thereby minimizing the height of the apparatus.

MODE FOR INVENTION

Provided is a radiotherapy apparatus for an animal that includes a treatment part including an accommodation space in which the animal is placed, an irradiation part including an electron generator and a linear accelerator that is coupled to one side of the electron generator and is disposed in a direction perpendicular to the treatment part and that emits radiation toward the treatment part, and an image acquisition part that is located at a preset interval from the treatment part along an irradiation direction of the radiation and that obtains an image of an irradiation area when the radiation is applied, in which the radiation has an output of 1 MeV to 2 MeV so as to be applied to a diseased part located within a predetermined distance range from epidermis of the animal.

With respect to terms used in the present disclosure, general terms currently and widely used are selected in view of functions in the present disclosure. However, the terms may vary depending on intentions of technicians in the related art or judicial precedents, an advent of new technology, etc. In specific cases, terms may be arbitrarily chosen by an applicant, and in this case, definitions thereof will be described in detail in the corresponding description of the present disclosure. Accordingly, the terms used in the present disclosure should not necessarily be construed as simple names of the terms, but be defined based on meanings of the terms and overall contents of the present disclosure.

Throughout the specification, when a portion includes a component, it may mean that the portion does not exclude another component unless specifically described to the contrary, but may further include another component. Furthermore, the terms "unit" and "module" described in the specification indicate a unit for processing at least one function or operation, which may be implemented by hardware, software or a combination thereof.

In addition, connecting lines, or connectors shown in various figures are intended to represent functional relationships and/or physical or logical couplings between various elements. It should be noted that many alternative or additional functional relationships, physical connections, or logical connections may be present in a practical device.

Hereinafter, embodiments of the present disclosure will be described in detail with reference to the accompanying drawings such that those skilled in the art to which the present disclosure pertains can readily carry out the present disclosure. However, the present disclosure may be implemented in various different forms and is not limited to the embodiments described herein.

Hereinafter, embodiments of the present disclosure will be described in detail with reference to the accompanying drawings.

Figure 1:
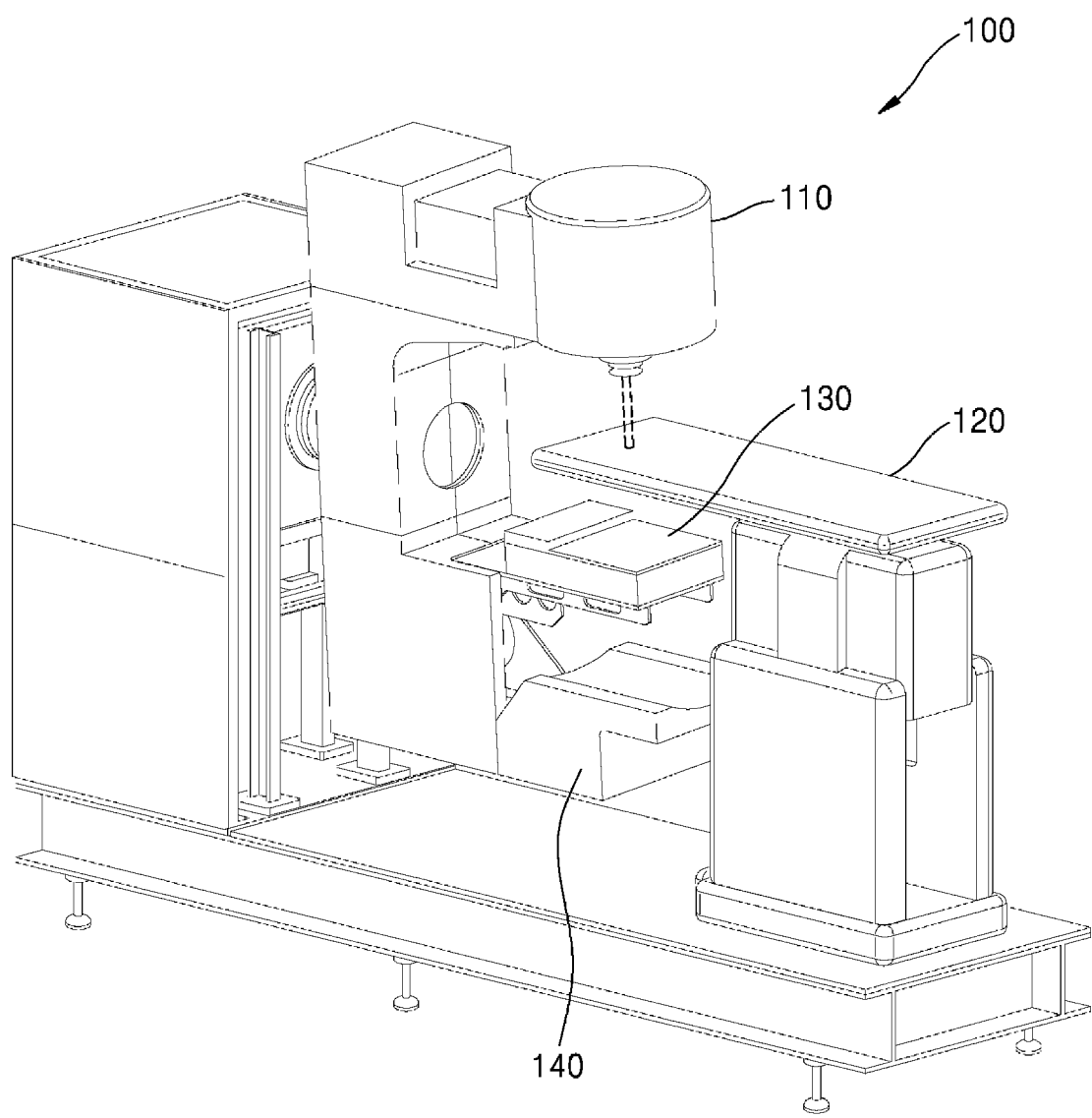
FIG. 1 is a view illustrating a radiotherapy apparatus according to an embodiment.

FIG. 1 is a view illustrating a radiotherapy apparatus according to an embodiment.

Referring to FIG. 1, the radiotherapy apparatus for an animal 100 may include an irradiation part 110, a treatment part 120, an image acquisition part 130, and a beam stopper 140. A more specific description thereabout will be given below.

Radiotherapy is a therapy for treating a tumor by intensively applying high-dose radiation to the tumor. A treatment technology for concentrating radiation on a tumor while minimizing damage to a surrounding normal organ, a precise radiotherapy apparatus, and various image identification devices are necessarily required for successful radiotherapy.

In particular, when a radiotherapy apparatus for a human body is used for radiotherapy for an animal, available energy is greater than required energy so that a surrounding organ may be affected, and the size of the radiotherapy apparatus may also be much larger than necessary, which may be inefficient. Accordingly, for more efficient radiotherapy for an animal, it is necessary to appropriately adjust the magnitude of energy and the size of a treatment apparatus.

Meanwhile, only components related to this embodiment are illustrated in the radiotherapy apparatus of FIG. 1. Accordingly, it will be understood by those skilled in the art related to this embodiment that other general purpose components other than the components illustrated in FIG. 1 may be further included in the radiotherapy apparatus. For example, it is apparent that a power supply (not illustrated) that supplies electric power to the irradiation part 110 and the like, at least one electrical connector (not illustrated) for electrical connection between the power supply and other parts requiring electric power, and the like may be included in the radiotherapy apparatus.

Specifically, the treatment part 120 may form an accommodation space in which an animal is placed for treatment of the animal. As illustrated in FIG. 1, the accommodation space at the top of the treatment part 120 may have a quadrangular shape. However, without being limited thereto, the accommodation space may have various sizes and shapes depending on the shape of the animal requiring treatment, and the like.

Furthermore, although not illustrated, the treatment part 120 may include a fixing part configured to fix the animal. Radiotherapy is a therapy for treating a tumor by intensively applying high-dose radiation to the tumor, and therefore for successful radiotherapy, it is necessary to concentrate the radiation on the tumor while minimizing damage to a surrounding normal organ. Accordingly, the fixing part may restrict a movement of the animal to enable the radiation to be concentrated on a desired place.

In addition, the treatment part 120 may include a movement device for a movement of the treatment part 120. As described above, a movement of the treatment part 120 may be required for successful radiotherapy on an accurate part. Without being limited to an up/down or left/right movement, the movement device of the treatment part 120 may be able to move while having an angle change between the treatment part 120 and a parallel surface of the ground. Specifically, the treatment part 120 may be capable of both rotary motion and translational motion in a horizontal direction and a vertical direction with respect to the parallel surface of the ground. Accordingly, the movement device may be configured to move the treatment part 120 in a desired direction with respect to radiation generated from the irradiation part 110.

The irradiation part 110 may emit X-rays, gamma rays, high-energy electrons, high-energy protons, or other high-energy fine particles. Furthermore, the irradiation part 110 may include any one of an X-ray generation device, a radioactive isotope source, or a linear accelerator. Alternatively, the irradiation part 110 may receive and emit a high-energy particle beam generated by accelerating particles in a particle accelerator provided outside the radiotherapy apparatus 100. For example, the irradiation part 110 may be implemented with a collimator. When the collimator is used, the irradiation part 110 is able to internally change the form of a beam, thereby enabling more efficient radiation energy transfer.

For example, the irradiation part 110 may include an electron generator and a linear accelerator. When electrons are allowed to flow from the electron generator to the linear accelerator, the electrons may obtain gradually increasing energy while passing through the linear accelerator. The linear accelerator may be coupled to one side of the electron generator and may be disposed in a direction perpendicular to the treatment part 120. When the linear accelerator is disposed in the direction perpendicular to the treatment part 120, it specifically means that the linear accelerator may be disposed perpendicular to a plane extending from a flat surface of the treatment part 120 when the treatment part 120 is disposed parallel to the ground. In this case, the linear accelerator may be an X-band type accelerator that can be implemented to be more compact than a general linear accelerator. Due to this, the linear accelerator may contribute to compactness of the radiotherapy apparatus. For example, in general, a linear accelerator used in an existing radiotherapy apparatus has a length of about 1 m and is disposed parallel to the surface of the ground. However, the linear accelerator of the present disclosure has a length of about 10 cm and is disposed in the direction perpendicular to the treatment part 120 as described above. Accordingly, the linear accelerator of the present disclosure may contribute to compactness of the radiotherapy apparatus.

Meanwhile, a gantry may be formed on one side surface of the irradiation part 110. The gantry may rotate 180° in a forward direction or a backward direction. That is, the gantry is formed such that the irradiation part 110 and the image acquisition part 130 are rotatable.

The image acquisition part 130 may be located at a preset interval from the treatment part 120 along an irradiation direction of radiation and may obtain an image of an irradiation area when the radiation is applied. For example, the image acquisition part 130, may be a kind of image sensor which obtains an image by detecting radiation and converting the detected radiation to an electrical signal.

Specifically, the image acquisition part 130 may be equipment for obtaining an image and may allow the position of a diseased part of the animal and an irradiation position of the treatment apparatus to be in alignment with each other before radiotherapy.

As an embodiment of the image acquisition part 130, a video-based electronic portable image device may be required to determine whether the position of a diseased part is correct or not, before radiation is applied to a subject. Specifically, during radiotherapy using radiation, to identify the position of the diseased part, the video-based electronic portable image device may obtain an image by detecting the radiation passing through the subject and converting the detected radiation to an electrical signal. Accordingly, the radiation may be accurately applied to the position of the diseased part.

Meanwhile, the video-based electronic portable image device may further include a reflecting mirror. Radiation emitted from the irradiation part 110 may be reflected through the reflecting mirror after passing through the animal on the treatment part 120. The reflected radiation may be changed to visible light by a scintillator, and the converted visible light may be detected through a camera, an optical sensor, or the like, and a user may monitor the visible light through display equipment.

However, a conventional video-based electronic portable image device has a drawback in that the entire device size increases due to the position of a reflecting mirror that is fixed at an angle of 45° to minimize distortion of an image.

In contrast, because the radiotherapy apparatus of the present disclosure is characterized by being made more compact than a general radiotherapy apparatus, the existing video-based electronic portable image device is not suitable to be included in the radiotherapy apparatus of the present disclosure. Accordingly, a contribution to compactness of the radiotherapy apparatus may be made by constructing a compact video-based image acquisition device by decreasing the height of the image acquisition part 130 by setting the angle of the reflecting mirror, which is included in the image acquisition part 130 of the present disclosure, to 45° or less with respect to a parallel surface of the ground.

However, an image obtained by this method has a problem in that distortion of the image may occur. To solve this problem, a distorted image may need to be corrected by using a separate image correction program.

The beam stopper 140 may interrupt leakage of radiation. Specifically, when radiation emitted by the irradiation part 110 passes through any one of the treatment part 120 or the image acquisition part 130, it is necessary to prevent leakage of the radiation.

To achieve this, the beam stopper 140 may be located to be spaced apart from the image acquisition part 130 along the irradiation direction of the radiation. As described above, the radiation is emitted from the irradiation part 110 toward the treatment part 120, and the image acquisition part 130 is located along the irradiation direction. Specifically, the irradiation part 110, the treatment part 120, the image acquisition part 130, and the beam stopper 140 may be located in said order.

Meanwhile, although not illustrated in the drawing, the radiotherapy apparatus 100 according to an embodiment of the present disclosure may further include an error correction device (not illustrated). The error correction device (not illustrated) may include a motor, an actuator, or the like. The error correction device (not illustrated) may be installed in at least one of the irradiation part 110 or the image acquisition part 130 and may be formed to be movable with respect to the X-axis, the Y-axis, or the Z-axis. The radiotherapy apparatus may include the error correction device (not illustrated) to correct a position error, thereby improving the accuracy of the radiotherapy apparatus.

Meanwhile, the irradiation part 110 may include a first collimator, an ion chamber, a lamp, a second collimator, and the like.

Hereinafter, structures of the ion chamber and the lamp included in the radiotherapy apparatus will be described in more detail with reference to FIG. 2.

Figure 2:
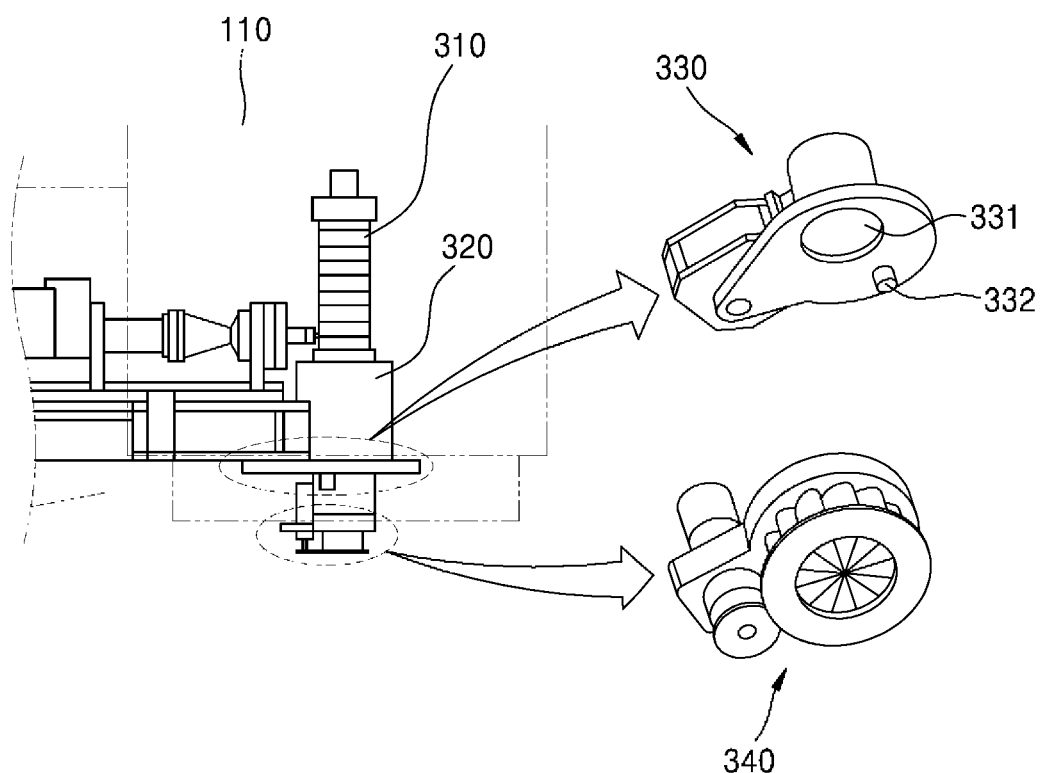
FIG. 2 is a view specifically illustrating the radiotherapy apparatus according to an embodiment.

FIG. 2 is a view specifically illustrating the radiotherapy apparatus according to an embodiment.

Referring to FIG. 2, the irradiation part 110 of the present disclosure may include the linear accelerator 310, the first collimator 320, the ion chamber 331, the lamp 332, the second collimator 340, and the like. A specific description of the linear accelerator 310 is the same as the description of the above-described components and therefore will be omitted. Meanwhile, only components related to this embodiment are illustrated in the radiotherapy apparatus of FIG. 2. Accordingly, it will be understood by those skilled in the art related to this embodiment that other general purpose components other than the components illustrated in FIG. 2 may be further included in the radiotherapy apparatus.

The ion chamber 331 may measure the output dose of a radiation beam. Specifically, when radiation enters the ion chamber, gas molecules in the ion chamber are excited to form ion pairs of a positive ion and a negative ion. At this time, current or voltage may be detected by applying an appropriate electric field to electrodes and collecting ions on the electrodes. Furthermore, the lamp 332 may be used to identify an irradiation area of radiation applied.

According to the related art, an ion chamber and a lamp used in the existing radiotherapy apparatus are disposed in a vertical structure, and therefore a large space for installation is required. In contrast, referring to FIG. 2, the ion chamber 331 and the lamp 332 included in the radiotherapy apparatus may be implemented on the same plane. Due to this, the ion chamber 331 and the lamp 332 may contribute to compactness of the radiotherapy apparatus.

The irradiation part 110 of the present disclosure may further include the first collimator 320, the second collimator 340, and the like.

In an embodiment, the collimators may be multi-leaf collimators. Specifically, the multi-leaf collimators are connected to the irradiation part 110 that applies radiation for treatment to a part to be treated and are used to allow the radiation to be applied to only the part to be treated.

Specifically, the first collimator 320 may determine the radiation range of a radiation beam emitted. Furthermore, the second collimator 340 may freely set the magnitude of the radiation beam. To achieve this, in the case of the second collimator 340, a pin-hole collimator having a driving method that is the same as the principle of a camera aperture may be used.

Figure 3:
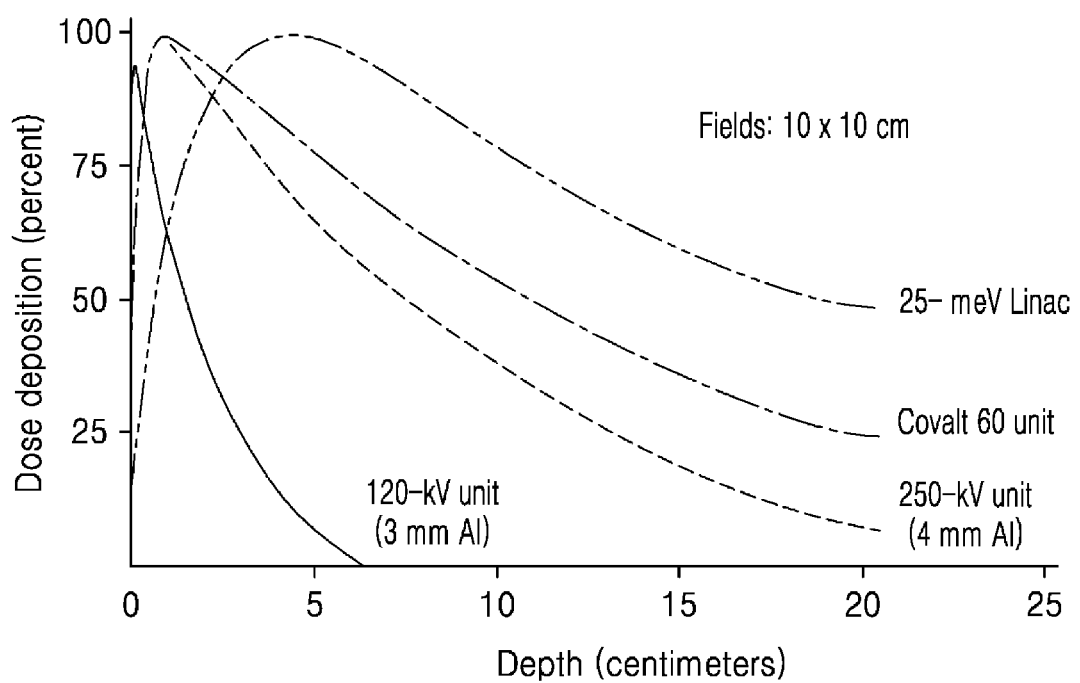
FIG. 3 is a view illustrating an effect of a low-energy spectrum according to an embodiment.

FIG. 3 is a view illustrating an effect of a low-energy spectrum according to an embodiment.

FIG. 3 illustrates dose deposition versus depth for energies of radiations. Referring to FIG. 3, the doses decrease depending on the depths to which the radiations penetrate. At this time, as the energy of radiation emitted becomes higher, a higher dose of radiation is delivered to an internal location, and thus efficiency in treatment is improved.

In contrast, as the energy of radiation emitted becomes lower, a lower dose of radiation is delivered to the internal location, and thus the radiation has characteristics unsuitable for treatment of a deep place. However, as the energy of radiation emitted becomes lower, the radiotherapy apparatus can be made compact, and there is an advantage in terms of economic efficiency. Considering that animal cancer frequently occurs in epidermis in a current clinical practice, it is necessary to select an appropriate energy spectrum.

First, in a case of a high-energy (6 MeV) radiotherapy apparatus, as energy becomes higher, not only photon rays but also neutrons are generated when radiation is generated, and a high shielding level for the neutrons is required. In ensuring and operating a space for equipment installation, there may be economic costs. Accordingly, in a case of performing radiotherapy on a medium-sized animal, using a high-energy spectrum may be inefficient, which may cause a problem in popularization of a radiotherapy apparatus for an animal.

Second, a 60-Co (1.25 MeV) radiotherapy apparatus using gamma rays may require lower operating costs and a lower shielding level than a high-energy radiotherapy apparatus. In contrast, economic costs for safety management and security are increasing due to an increase in the risk of terrorism against an isotope source, and when a dose rate is reduced due to the half-life of an isotope, there may be replacement costs according to that. Furthermore, the 60-Co (1.25 MeV) radiotherapy apparatus may have a problem in that a penumbra exists, as compared with a radiotherapy apparatus based on a linear accelerator.

Third, a KeV unit low-energy radiotherapy apparatus using an X-ray tube method has a maximum dose point on epidermis and thus has efficiency in treating a surface, but may have a problem in that efficiency decreases when a tumor located at an internal location of a medium-sized animal is treated with radiation. Furthermore, radiation of the KeV unit has a larger penumbra area than radiation of the MeV unit, and therefore there may be a problem in that an uncertain area exists. Specifically, in a case of the KeV unit low-energy radiotherapy apparatus, it is unclear whether energy is transferred to a depth of 10 cm or more, and therefore there is a problem in that it is necessarily required to verify the dose for an irradiation surface.

Accordingly, in the present disclosure, considering this point, it is necessary to select an area having energy lower than high energy (6 MeV) and having a small uncertain penumbra area. That is, a radiotherapy apparatus having energy between 1 MeV and 2 MeV has critical significance in treatment of a medium-sized animal. In particular, by applying radiation having an output of 1 MeV to 2 MeV, the radiotherapy apparatus may allow the radiation to be applied not only to the epidermis of an animal but also to a diseased part located within a predetermined distance range from the epidermis. The predetermined distance may range from 10 cm to 20 cm. Specifically, in a case of energy between 1 MeV and 2 MeV, a penumbra area does not appear within an appropriate thickness range of 10 cm to 20 cm in the treatment of a medium-sized animal, and a treatment apparatus may be appropriately configured in terms of economy and space, as compared with a high-energy radiotherapy apparatus.

The above description of the present disclosure is provided for the purpose of illustration, and it would be understood by those skilled in the art that various changes and modifications can be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined not by the detailed description, but by the claims and their equivalents, and all variations within the scope of the claims and their equivalents are to be construed as being included in the present disclosure.

The invention claimed is:

1. A radiotherapy apparatus for an animal, comprising:
   a treatment part including an accommodation space for placing an animal;
   an irradiation part including an electron generator and a linear accelerator coupled to one side of the electron generator and disposed in a direction perpendicular to the treatment part, the linear accelerator being configured to emit radiation toward the treatment part; and
   an image acquisition part located at a preset interval from the treatment part along an irradiation direction of the radiation and configured to obtain an image of an irradiation area when the radiation is applied,
   a beam stopper located to be spaced apart from the image acquisition part along the irradiation direction of the radiation to interrupt leakage of the radiation through at least one of the treatment part or the image acquisition part,
   wherein the radiation has an output of 1 MeV to 2 MeV so as to be applied to a diseased part located within a predetermined distance range from epidermis of the animal, the irradiation part, the treatment part, the image acquisition part, and the beam stopper are located in said order along the irradiation direction of radiation, the irradiation part further includes a first collimator and a second collimator configured to adjust the irradiation area of the radiation, the first collimator is a multi-leaf collimator, and the second collimator is a pin-hole collimator.

2. The radiotherapy apparatus of claim 1, wherein the irradiation part further includes a lamp configured to identify the irradiation area when the irradiation is applied and an ion chamber configured to measure an output of the radiation, and wherein the lamp and the ion chamber are located on the same plane.

3. The radiotherapy apparatus of claim 1, wherein the treatment part is movable in a horizontal direction and a vertical direction with respect to a parallel surface of the ground.

4. The radiotherapy apparatus of claim 1, wherein the predetermined distance range is a range of 10 cm to 20 cm.

5. The radiotherapy apparatus of claim 1, wherein the first collimator determines a radiation range of the radiation, and the second collimator sets a magnitude of the radiation.

6. The radiotherapy apparatus of claim 1, comprising:

an error correction device to correct a position of one of the irradiation part, the image acquisition part and a combination thereof.

\* \* \* \* \*